US012727744B2

(12) United States Patent
Otake et al.

(10) Patent No.: US 12,727,744 B2
(45) Date of Patent: Sep. 8, 2026

(54) BEAM-SHAPING LENS, BEAM-SHAPING ELEMENT, LIGHT SOURCE DEVICE FOR AN ENDOSCOPE, AND ENDOSCOPE

(71) Applicants: Sumita Optical Glass, Inc., Saitama (JP); NIREC Corporation, Kochi (JP)

(72) Inventors: Jun Otake, Saitama (JP); Hiroki Watanabe, Saitama (JP); Eiji Ototsuki, Saitama (JP); Yuichi Takenaga, Kochi (JP)

(73) Assignees: Sumita Optical Glass, Inc., Saitama (JP); NIREC Corporation, Kochi (JP)

( * ) Notice: Subject to any disclaimer, the term of this patent is extended or adjusted under 35 U.S.C. 154(b) by 205 days.

(21) Appl. No.: 18/690,742

(22) PCT Filed: Oct. 5, 2022

(86) PCT No.: PCT/JP2022/037353

§ 371 (c)(1),
(2) Date: Mar. 11, 2024

(87) PCT Pub. No.: WO2023/058700

PCT Pub. Date: Apr. 13, 2023

(65) Prior Publication Data

US 2025/0098943 A1 Mar. 27, 2025

(30) Foreign Application Priority Data

Oct. 6, 2021 (JP) ................................ 2021-164970

(51) Int. Cl.
*A61B 1/00* (2006.01)
*A61B 1/06* (2006.01)
(Continued)

(52) U.S. Cl.
CPC .......... *A61B 1/0019* (2013.01); *A61B 1/0638* (2013.01); *A61B 1/0661* (2013.01);
(Continued)

(58) Field of Classification Search
CPC ....................... G02B 27/0927; G02B 27/0955; G02B 27/30; G02B 23/2461; A61B 1/0661;
(Continued)

(56) References Cited

U.S. PATENT DOCUMENTS

2012/0083656 A1* 4/2012 Kuroda .................. A61B 1/063 600/165
2012/0310047 A1* 12/2012 Kasamatsu .......... A61B 1/0638 600/178

(Continued)

FOREIGN PATENT DOCUMENTS

CN 102805605 A 12/2012
CN 111323926 A 6/2020

(Continued)

OTHER PUBLICATIONS

"Reshaping of a Divergent Elliptical Gaussian Laser Beam Into a Circular, Collimated, and Uniform Beam With Aspherical Lens Design"—Serkan et al., IEEE Sensors Journal, vol. 9, No. 1, Jan. 2009 (Year: 2009).*

(Continued)

*Primary Examiner* — Mainul Hasan
(74) *Attorney, Agent, or Firm* — KENJA IP LAW PC

(57) ABSTRACT

A beam-shaping lens includes a first surface including a smooth-shaped concave surface; and a second surface including a convex surface substantially similar in shape to the concave surface. The beam-shaping lens converts a first light beam that is parallel light incident on the first surface and having a light intensity distribution that continuously increases from an outer periphery toward a center, into a second light beam that has a flatter light intensity distribution than that of the first light beam.

9 Claims, 7 Drawing Sheets

(51) Int. Cl.

| | |
|---|---|
| ***A61B 1/07*** | (2006.01) |
| ***G02B 3/04*** | (2006.01) |
| ***G02B 15/14*** | (2006.01) |
| ***G02B 27/09*** | (2006.01) |
| ***G02B 27/30*** | (2006.01) |

(52) U.S. Cl.
CPC .................. *A61B 1/07* (2013.01); *G02B 3/04* (2013.01); *G02B 15/1425* (2019.08); *G02B 27/0927* (2013.01); *G02B 27/30* (2013.01)

(58) Field of Classification Search
CPC .............. A61B 1/0019; A61B 1/00188; A61B 1/00096; A61B 1/00
See application file for complete search history.

(56) References Cited

U.S. PATENT DOCUMENTS

| | | | | |
|---|---|---|---|---|
| 2015/0327756 | A1* | 11/2015 | Yamamoto | A61B 1/0017 362/558 |
| 2016/0161751 | A1 | 6/2016 | Kiontke et al. | |
| 2017/0010456 | A1* | 1/2017 | Gopinath | G02B 3/14 |
| 2020/0187766 | A1 | 6/2020 | Zalevsky et al. | |

FOREIGN PATENT DOCUMENTS

| | | | | |
|---|---|---|---|---|
| CN | 112773302 | A | 5/2021 | |
| CN | 113466976 | A | 10/2021 | |
| JP | H09295817 | A | 11/1997 | |
| JP | H10319212 | A | 12/1998 | |
| JP | 2003084214 | A * | 3/2003 | G02B 13/24 |
| JP | 2006145676 | A | 6/2006 | |
| JP | 2007290903 | A | 11/2007 | |
| JP | 2009240560 | A | 10/2009 | |
| JP | 2012042513 | A | 3/2012 | |
| JP | 2012080949 | A | 4/2012 | |
| JP | 2012245285 | A | 12/2012 | |
| JP | 2014008316 | A | 1/2014 | |
| JP | 2014206740 | A | 10/2014 | |
| JP | 2016002302 | A | 1/2016 | |
| JP | 2020062326 | A | 4/2020 | |

OTHER PUBLICATIONS

Dec. 20, 2022, International Search Report issued in the International Patent Application No. PCT/JP2022/037353.

Jun. 3, 2025, Notification of Reasons for Refusal issued by the Japan Patent Office in the corresponding Japanese Patent Application No. 2021-164970.

Sep. 9, 2025, the Extended European Search Report issued by the European Patent Office in the corresponding European Patent Application No. 22878568.9.

Apr. 9, 2024, International Preliminary Report on Patentability issued in the International Patent Application No. PCT/JP2022/037353.

Nov. 11, 2025, Notification of Reasons for Refusal issued by the Japan Patent Office in the corresponding Japanese Patent Application No. 2021-164970.

Jul. 22, 2026, Office Action issued by the China National Intellectual Property Administration in the corresponding Chinese Patent Application No. 202280060803.9.

* cited by examiner 10
21
212a
212b
211a
211b
213
22a
22b
22
L3
1B
L4
33
32
31
L2
1A
L1
11
12

BEAM-SHAPING LENS, BEAM-SHAPING ELEMENT, LIGHT SOURCE DEVICE FOR AN ENDOSCOPE, AND ENDOSCOPE

TECHNICAL FIELD

The present disclosure relates to a beam-shaping lens, a beam-shaping element, a light source device for an endoscope, and an endoscope.

BACKGROUND

In endoscopic diagnosis, general observation of the surface tissue is performed using white light, and fluorescence observation is performed using excited light in a particular wavelength range to observe fluorescence in deep inside the living body. For example, in PTLs 1 and 2, white light and laser light which is excitation light are combined in a light source device, which is used as a light source for endoscopy. Furthermore, PTL 3 proposes a method for reducing speckles in the illumination light in a light source device for an endoscope that utilizes bundled light from a plurality of laser light sources for fluorescence observation.

CITATION LIST

Patent Literature

[PTL 1] JP 2020-62326 A
[PTL 2] JP 2016-2302 A
[PTL 3] JP 2009-240560 A

SUMMARY

Technical Problem

In the meanwhile, in recent years, the wider angle of view of endoscopes has made it possible to observe a wider area of biological tissue. However, light sources such as LEDs (light emitting diodes) and lasers used for endoscopy have an intensity distribution where the intensity increases from the outer periphery towards the center. When endoscopic observation is attempted with a wide field of view using such light, the center of the field is bright while the outer peripheries are dim. Increasing the output of the light source to brighten the outer peripheries may lead to excessively high light intensity at the center, which may damage the biological tissues under observation. Therefore, with conventional light sources for endoscopes, it can be difficult to accurately observe biological tissues over a wide area without causing potential damage.

Therefore, an object of the present disclosure, made in view of these issues, is to provide a beam-shaping lens, a beam-shaping element, a light source device for an endoscope, and an endoscope including this light source device for an endoscope that can generate illumination light having more uniform light intensity distribution.

Solution to Problem

The present inventors have discovered that the aforementioned object can be achieved by using a beam-shaping lens that converts a first light beam having a light intensity distribution that continuously increases from an outer periphery toward a center, into a second light beam that has a flatter light intensity distribution than that of the incident light.

In other words, a beam-shaping lens that achieves the aforementioned object comprises a first surface comprising a smooth-shaped concave surface; and a second surface comprising a convex surface substantially similar in shape to the concave surface, the beam-shaping lens converting a first light beam that is parallel light incident on the first surface and having a light intensity distribution that continuously increases from an outer periphery toward a center, into a second light beam that has a flatter light intensity distribution than that of the first light beam.

Preferably, in the aforementioned beam-shaping lens, the first surface and the second surface are axisymmetric around the same central axis, and the first surface and the second surface are configured such that a ray of light incident on the first surface in a direction parallel to the central axis exits from the second surface in a direction parallel to the central axis.

Preferably, in the aforementioned beam-shaping lens, the first surface and the second surface are flat at outer peripheries, and the concave surface and the convex surface are smoothly continuous to the outer peripheries of the first surface and the second surface, respectively.

Preferably, the beam-shaping lens is configured to convert the first light beam having a Gaussian or Lambertian light intensity distribution into the second light beam having a top hat-shaped light intensity distribution.

A beam-shaping element that achieves the aforementioned object comprises a plurality of beam-shaping lenses overlapping each other, the beam-shaping lenses comprising a first surface comprising a smooth-shaped concave surface and a second surface comprising a convex surface substantially similar in shape to the concave surface, the beam-shaping lens converting a first light beam that is parallel light incident on the first surface and having a light intensity distribution that continuously increases from an outer periphery toward a center, into a second light beam that has a flatter light intensity distribution than that of the first light beam.

A light source device for an endoscope that achieves the aforementioned object comprises a first light source unit; a first collimating optical system that converts light emitted from the first light source unit into a first light beam that is parallel light; and a first beam-shaping lens comprising a first surface comprising a smooth-shaped concave surface and a second surface comprising a convex surface substantially similar in shape to the concave surface, the first beam lens converting the first light beam incident on the first surface and having a light intensity distribution that continuously increases from an outer periphery toward a center, into a second light beam that has a flatter light intensity distribution than that of the first light beam.

Preferably, in the aforementioned light source device for an endoscope, the first collimating optical system comprises a zoom optical system comprising a first lens having a negative refractive power and a second lens having a positive refractive power, and configured to adjust positions of the first lens and the second lens in conjunction with each other.

Preferably, in the aforementioned light source device for an endoscope, the first light source unit comprises a plurality of light sources that emit light in the same wavelength range, a plurality of optical fibers that guide the light emitted from each of the light sources, and an optical fiber end retainer that aligns and retains emission side ends of the light of the plurality of optical fibers.

Preferably, the aforementioned light source device for the endoscope comprises a second light source that emits light in a wavelength range different from that of the first light source unit; a second collimating optical system that converts the light emitted from the second light source unit into a third light beam that is parallel light; a second beam-shaping lens comprising a third surface comprising a smooth-shaped concave surface and a fourth surface comprising a convex surface substantially similar in shape to the concave surface, the second beam-shaping lens converting the third light beam incident on the third surface and having a light intensity distribution that continuously increases from an outer periphery toward a center, into a fourth light beam that has a flatter light intensity distribution than that of the third light beam; a combining unit that combines the second light beam exiting from the first beam-shaping lens and the fourth light beam exiting from the second beam-shaping lens; and a focusing lens that couples the second light beam and the fourth light beam combined at the combining unit, into a light guide that guides the light to an endoscope.

Preferably, in the aforementioned light source device for an endoscope, the combining unit comprises a dichroic mirror.

Preferably, in the aforementioned light source device for an endoscope, the first light source unit comprises a white light source and the second light source unit comprises an excitation light source for fluorescent observation.

Preferably, in the aforementioned light source device for an endoscope, the second collimating optical system comprises a zoom optical system comprising a first lens having a negative refractive power and a second lens having a positive refractive power, and configured to adjust positions of the first lens and the second lens in conjunction with each other.

Preferably, in the aforementioned light source device for an endoscope, the second light source unit comprises a plurality of light sources that emit light in the same wavelength range, a plurality of optical fibers that guide the light emitted from each of the light sources, and an optical fiber end retainer that aligns and retains emission side ends of the light of the plurality of optical fibers.

Preferably, in the aforementioned light source device for an endoscope, a combined focal length of the second collimating optical system is within 10 mm, the combining unit permits a deviation of ±5° or less from a specified incident direction of the fourth light beam exiting from the second beam-shaping lens, and an aperture diameter in the optical fiber end retainer accommodating the emission side ends of the plurality of optical fibers is 1.2 mm or less.

An endoscope that achieves the aforementioned object comprises a light source device for an endoscope comprising: a first light source unit; a first collimating optical system that converts light emitted from the first light source unit into a first light beam that is parallel light; and a first beam-shaping lens comprising a first surface comprising a smooth-shaped concave surface and a second surface comprising a convex surface substantially similar in shape to the concave surface, the first beam lens converting the first light beam incident on the first surface and having a light intensity distribution that continuously increases from an outer periphery toward a center, into a second light beam that has a flatter light intensity distribution than that of the first light beam

Advantageous Effect

According to the present disclosure, a first light beam that is parallel light incident on the first surface and having a light intensity distribution that continuously increases from an outer periphery toward a center is converted into a second light beam that has a flatter light intensity distribution than that of the first light beam, illumination light having a more uniform light intensity distribution can be generated.

DETAILED DESCRIPTION

Hereinafter, an embodiment of the present disclosure will be described with reference to the drawings. The figures used in the following description are schematic. The dimensions and proportions on the drawings may not necessarily correspond exactly to the actual ones.

Beam-Shaping Lens

Figure 1:
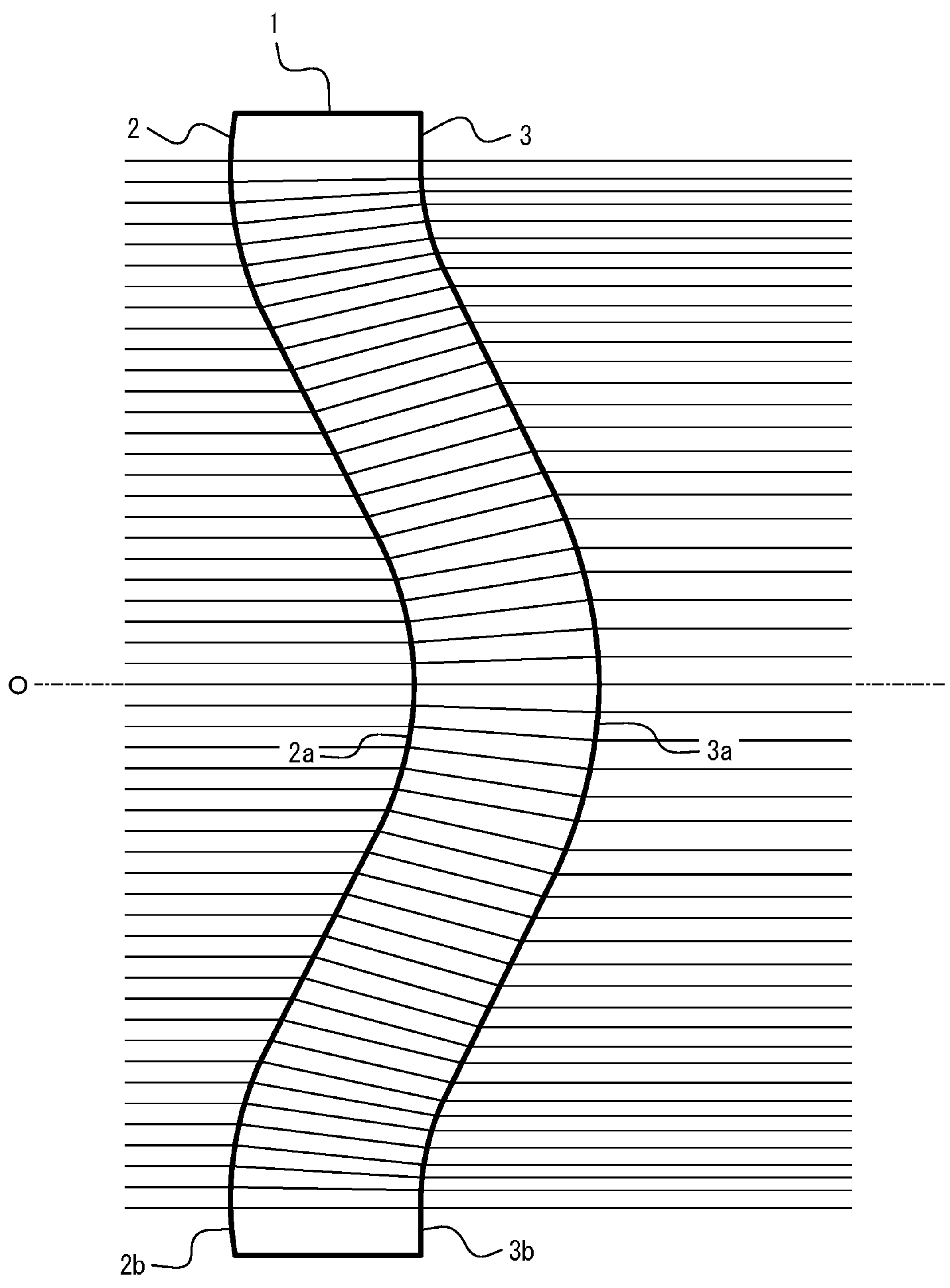
FIG. 1 is a cross-sectional view illustrating the shape of a beam-shaping lens according to one embodiment, together with the trajectories of parallel rays of light passing through the beam-shaping lens.

FIG. 1 is a cross-sectional view of a beam-shaping lens 1 according to one embodiment. The beam-shaping lens 1 has a circular outer profile, for example, when viewed along the optical axis O. The beam-shaping lens 1 is made of a material such as glass or resin that allows the transmission of light at the desired wavelength. The beam-shaping lens 1 has a first surface 2 and a second surface 3. The first surface 2 may be the incident side of the light. The second surface 3 may be the emission side of the light. The first surface 2 has a smooth-shaped concave surface 2*a*. The second surface 3 has a convex surface 3*a* substantially similar in shape to the concave surface 2*a*. The first surface 2 and the second surface 3 have shapes that are axisymmetric around the optical axis O, with the optical axis O as the central axis.

The outer periphery 2*b* of the first surface 2 and the outer periphery 3*b* of the second surface 3 are formed as flat surfaces orthogonal to the optical axis O. The concave surface 2*a* and the outer periphery 2*b* of the first surface 2 are smoothly continuous. In addition, the convex surface 3*a* of the second surface 3 and the outer periphery 3*b* are smoothly continuous.

FIG. 1 illustrates the trajectories of rays of light incident on the first surface 2 from a direction parallel to the optical axis O. As illustrated in FIG. 1, rays of light passing on the optical axis O and rays of light incident on the outer periphery 2*b* incident on the first surface 2 vertically and exit from the second surface 3 vertically. The trajectories of these rays of light are not deflected as they pass through the beam-shaping lens 1. On the other hand, rays of light incident on the concave surface 2*a* of the first surface 2 (except on the optical axis O) are refracted so as to be distant from the optical axis O by the first surface 2 and incident on the beam-shaping lens 1. The rays of light traveling in the beam-shaping lens 1 are refracted in a direction parallel to the optical axis O by the convex surface 3*a* of the second surface 3 and exit from the beam-shaping lens 1. The first surface 2 and the second surface 3 of the beam-shaping lens 1 may thus be designed so that rays of light incident on the first surface 2 from a direction parallel to the optical axis O exit from the second surface 3 in a direction parallel to the optical axis O.

As illustrated in FIG. 1, a light beam of parallel light incident on the first surface 2 from a direction parallel to the optical axis O exits from the second surface 3 as a light beam of parallel light so that the light intensity distribution is decreased in the center portion in the vicinity of the optical axis O and the light intensity distribution is increased in the portion in the vicinity of the outer periphery 3*b* distant from the optical axis O. In addition, when the outer diameter of the incident light beam is large enough to reach the outer periphery 2*b* of the first surface 2 of the beam-shaping lens 1, the diameter of the light beam does not change as it passes through the beam-shaping lens 1. Note that in the present disclosure, "parallel light" means that all rays of light in a beam are parallel to other rays of light.

Figure 2:
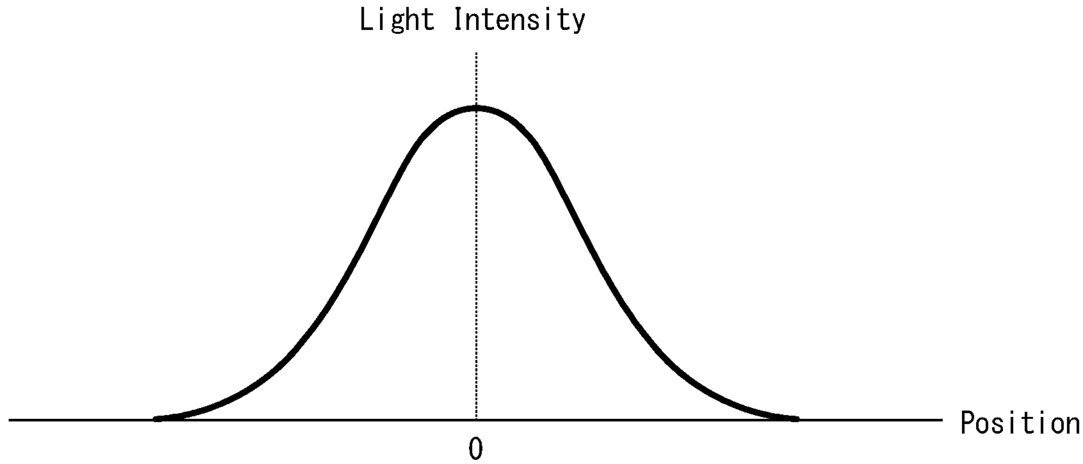
FIG. 2 is a diagram illustrating one example of the light intensity distribution of light incident on the beam-shaping lens.

FIG. 2 illustrates a Gaussian light intensity distribution as one example of the light intensity distribution of a light beam incident on the beam-shaping lens 1. The horizontal axis represents the position with the center of the light beam as the origin. The vertical axis represents the light intensity. In a Gaussian light intensity distribution, the intensity of the light beam increases from the outer periphery toward the center. In general, light emitted from a laser source has a Gaussian light intensity distribution as illustrated in FIG. 2. Moreover, light emitted from a multi-mode fiber has a shape where the center of a Gaussian intensity distribution is collapsed. On the other hand, light emitted from an LED has a Lambertian light intensity distribution. In a Lambertian light intensity distribution, the light intensity also increases from the outer periphery toward the center.

Figure 3:
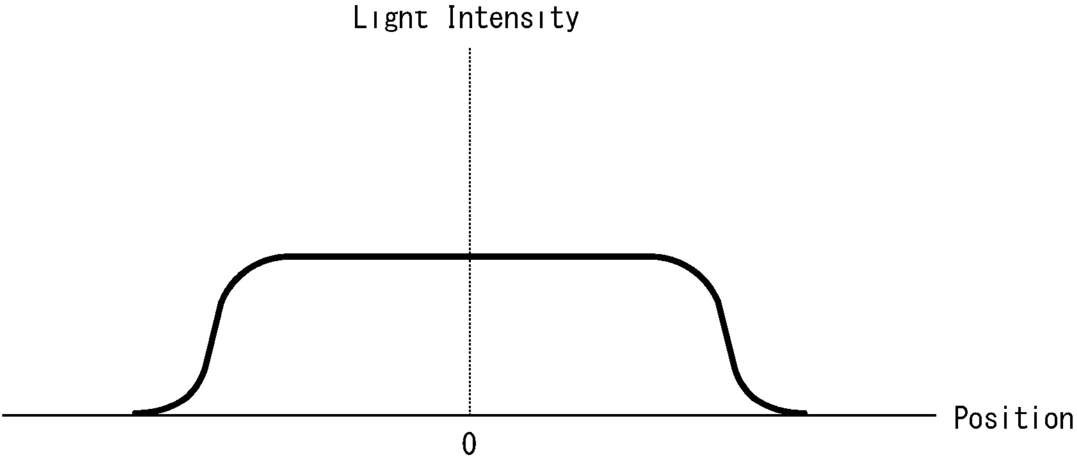
FIG. 3 is a diagram illustrating one example of the light intensity distribution after light with the light intensity distribution illustrated in FIG. 2 passes through the beam-shaping lens.

FIG. 3 is a diagram illustrating one example of the light intensity distribution after a light beam with a Gaussian light intensity distribution illustrated in FIG. 2 passes through the beam-shaping lens 1. The vertical and horizontal axes in FIG. 3 are the same as in FIG. 2. The beam-shaping lens 1 decreases the light intensity in the center portion of the light beam and increases the light intensity in the outer peripheral portion. As a result, the light beam exiting the beam-shaping lens 1 has a flatter light intensity distribution in a top-hat shape. Flat light intensity distribution means that the light intensity distribution is more uniform. The light intensity distribution is nearly flat, at least in the region including the center through which the optical axis O passes. Accordingly, the light intensity distribution of the light beam exiting the beam-shaping lens 1 is closer to a uniform distribution than the light intensity distribution of the light beam incident on the beam-shaping lens 1.

The beam-shaping lens 1 may be configured as a lens with the shape of the first surface 2 and the second surface 3 designed taking into consideration the light intensity distribution of the incident light beam, the desired light intensity distribution of the exiting light beam, the refractive index of the material, and the like. The shape of the desired light intensity distribution of the exiting light is not limited to a flat top-hat shape. For example, when the inside of a living body is observed with an endoscope, the distance to the object to be observed is farther at the outer periphery than at the center. Thus, higher light intensity may be required at the outer periphery side than at the center of the light beam.

Since the concave surface 2*a* of the first surface 2 and the convex surface 3*a* of the second surface 3 are substantially similar in shape, the beam-shaping lens 1 can be manufactured by applying heat and pressure to a single piece of a resin or other transparent plate-like material, thereby causing it to bend. Accordingly, the beam-shaping lens 1 can be manufactured at a low cost.

Beam-Shaping Element

Figure 4:
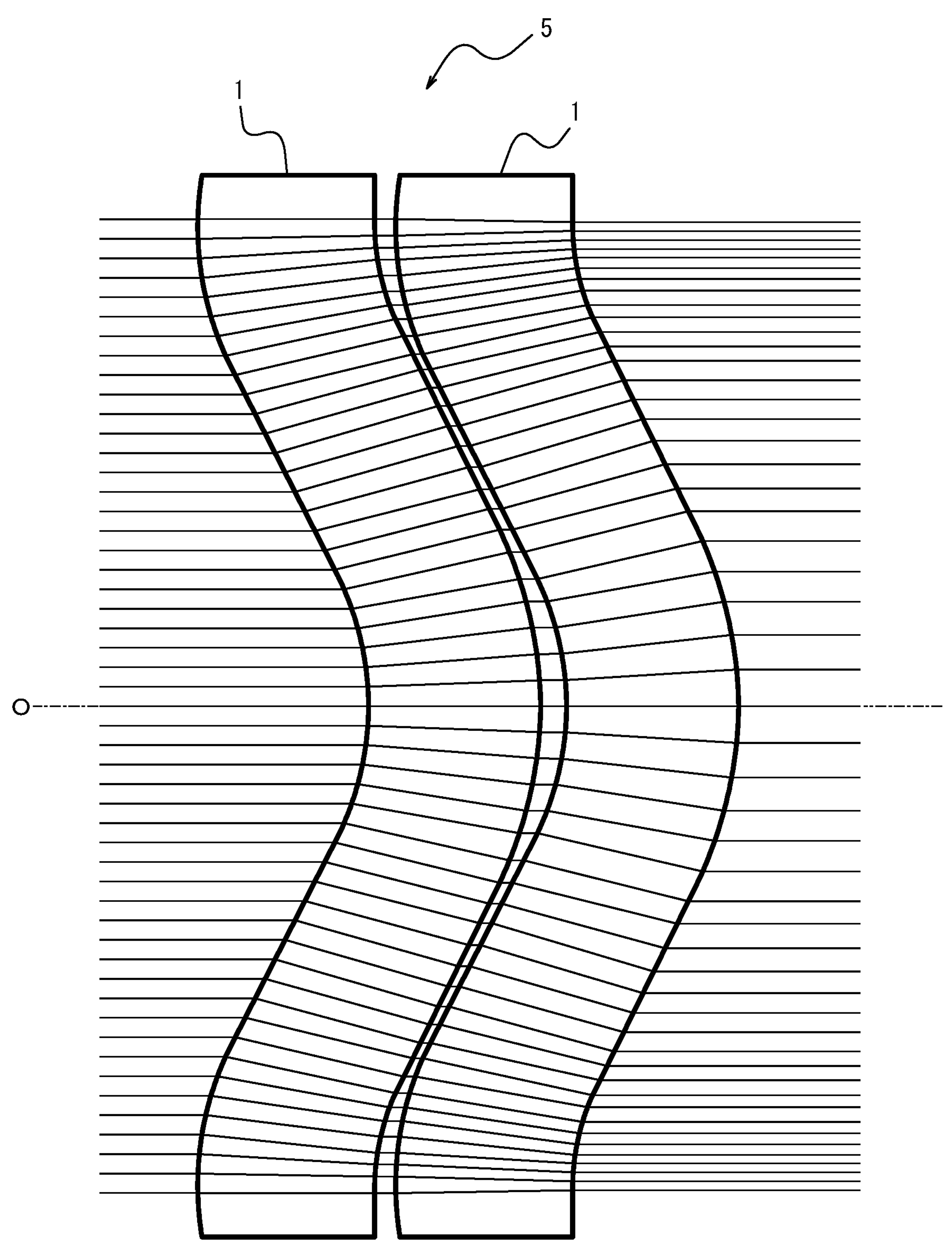
FIG. 4 is a diagram illustrating one example of a beam-shaping element configured from two beam-shaping lenses.

To obtain different light intensity distributions that are desired, a plurality of beam-shaping lenses 1 may be combined to form a beam-shaping element 5, as illustrated in FIG. 4. The plurality of beam-shaping lenses 1 are arranged to overlap each other so that their optical axes O coincide with each other. For example, a plurality of beam-shaping lenses 1 with a low conversion effect of the light intensity distribution may be prepared in advance, and the number of beam-shaping lens 1 used in combination may be determined based on the light intensity distribution of the incident light beam and the desired light intensity distribution of the exiting light beam.

Light Source Device for an Endoscope

Figure 5:
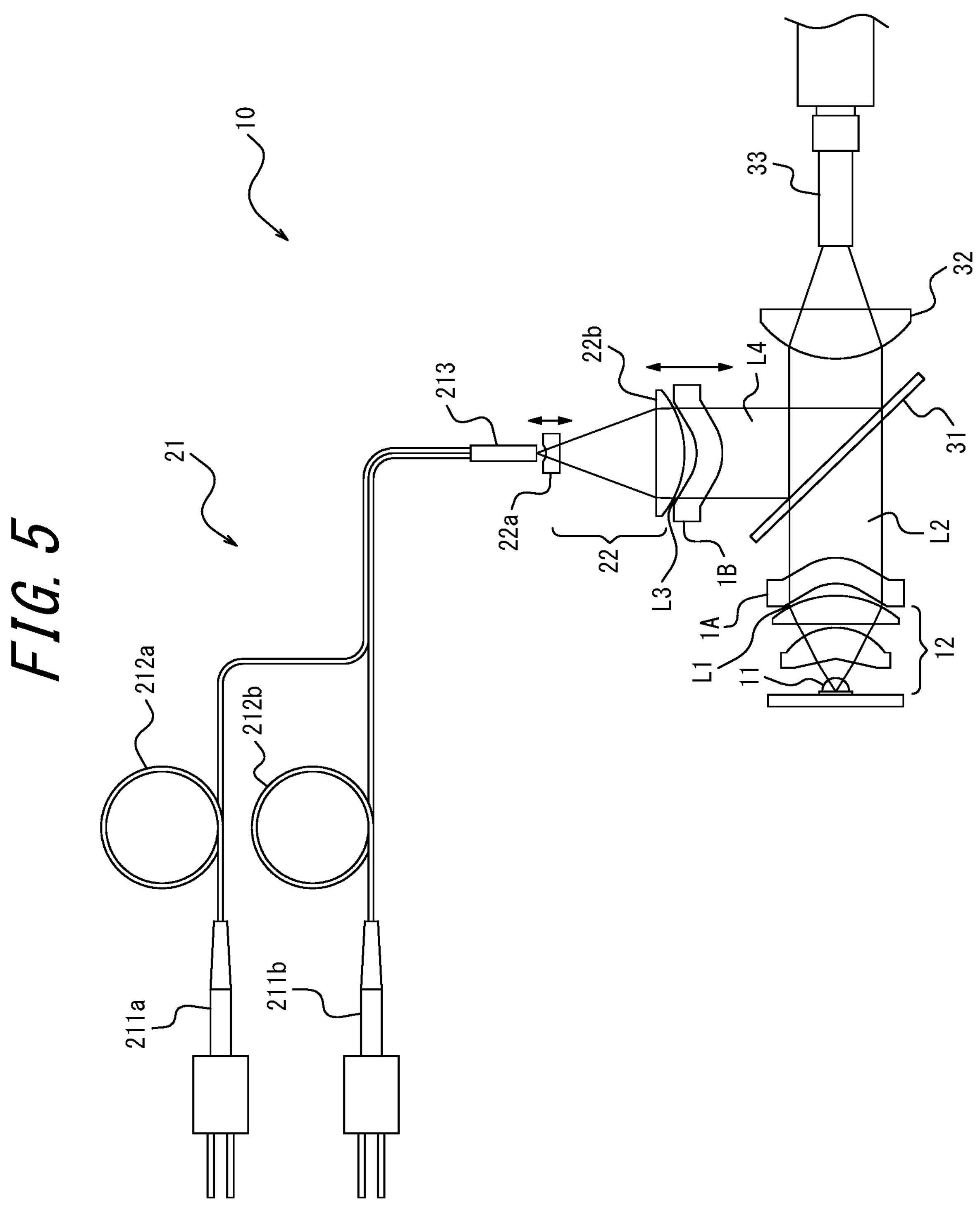
FIG. 5 is a diagram illustrating the schematic configuration of a light source device for an endoscope according to one embodiment.

Referring to FIG. 5, a light source device 10 for an endoscope including beam-shaping lenses 1 will be described. A light source device 10 for an endoscope is used as a light source for an endoscope that can perform both the diagnosis of the surface of biological tissues using white light and the observation of fluorescence deep inside the biological tissues using light of a particular wavelength range as excitation light.

The light source device 10 for an endoscope includes a first light source unit 11, a first collimating optical system 12, a first beam-shaping lens 1A, a second light source unit 21, a second collimating optical system 22, a second beam-shaping lens 1B, a dichroic mirror 31, and a focusing lens 32.

The first light source unit 11 is a white light source using a white LED, for example. The first collimating optical system 12 converts diverging white light emitted from the first light source unit 11 into a first light beam L1 that is parallel light. The first collimating optical system 12 may include one or more lenses. The first light beam L1 emitted from the first collimating optical system 12 has a light intensity distribution that continuously increases from the outer periphery to the center. A light intensity distribution that increases continuously from the outer periphery to the center is, for example, a Gaussian or Lambertian light intensity distribution.

The first beam-shaping lens 1A is a lens configured in the same manner as the beam-shaping lens 1 illustrated in FIG. 1. The first beam-shaping lens 1A converts the first light beam L1 into a second light beam L2 that is a parallel light with a flatter light intensity distribution than that of the first light beam L1. The second light beam L2 may have a flat light intensity distribution from the vicinity of the outer periphery of the second light beam L2 to the center.

The second light source unit 21 includes, for example, a first light source 211*a* and a second light source 211*b* as excitation light sources for fluorescence observation. The first light source 211*a* and the second light source 211*b* emit light in a specific wavelength range that excites the object to be observed. The first light source 211*a* and the second light source 211*b* are, for example, near-infrared lasers. In the present embodiment, multiple light sources that emit light of the same wavelength range are used to obtain light of sufficient intensity for fluorescent observation. Since the intensity of a single light source for fluorescence observation is often insufficient, multiple light sources for excitation light may be used in this manner. In addition, multiple light sources may also be provided as backup light sources. Note that the number of light sources included in the second light source unit 21 is not limited to two. One, three, or more light sources may be included in the second light source unit 21.

The second light source unit 21 further includes a first optical fiber 212*a* that guides light emitted from the first light source 211*a* and a second optical fiber 212*b* that guides light emitted from the second light source 211*b*. The first optical fiber 212*a* and the second optical fiber 212*b* can be multimode fibers.

Figure 6:
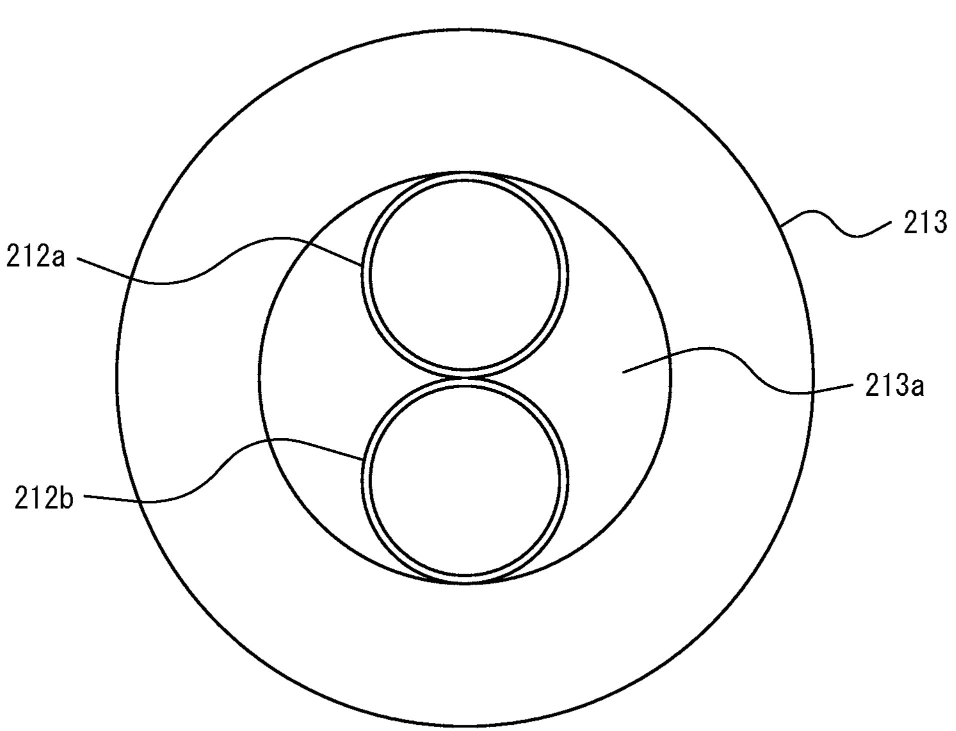
FIG. 6 is a diagram illustrating the emission side end face of a ferrule.

The second light source unit 21 further includes a ferrule 213 that aligns and retains the emission side ends of the first optical fiber 212*a* and the second optical fiber 212*b*. An example of the emission side end face of the ferrule 213 is illustrated in FIG. 6. The ferrule 213 is a cylindrical member made of, for example, ceramic such as zirconia or stainless steel, having a fiber aperture 213*a* in the center thereof for inserting the optical fibers. The ferrule 213 is the optical fiber end retainer. The laser light propagating through the first optical fiber 212*a* and the second optical fiber 212*b* exits from the fiber aperture 213*a* in the ferrule 213. The aperture diameter of the fiber aperture 213*a* of the ferrule 213 that accommodates the emission side ends of the first optical fiber 212*a* and the second optical fiber 212*b* is, for example, 1.2 mm or less and is much smaller than the diameter of the second beam-shaping lens 1B (for example, about 20 mm) in the subsequent stage.

Figure 7:
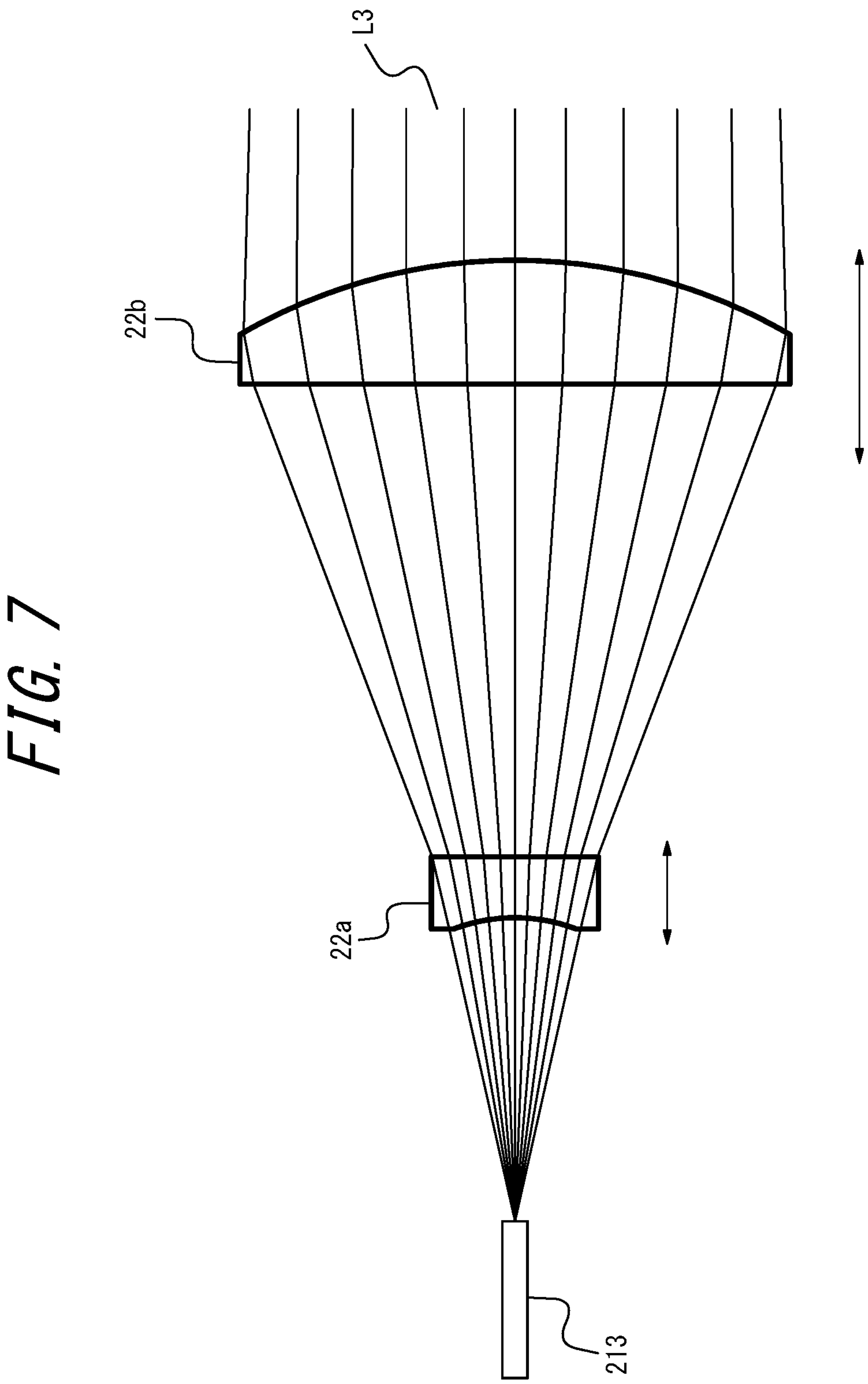
FIG. 7 is a diagram illustrating the action of the zoom optical system in FIG. 5.

The laser beam emitted from the ferrule 213 is converted into a third light beam L3 that is parallel light by the second collimating optical system 22. The second collimating optical system 22 includes a first lens 22*a* with negative refractive power and a second lens 22*b* with positive refractive power, as illustrated in FIG. 7. In the second collimating optical system 22, the third light beam L3 emitted from the second lens 22*b* can be changed in beam diameter while maintaining the light to be parallel light by displacing the first lens 22*a* and the second lens 22*b* in the optical axis direction in conjunction with each other. In other words, the second collimating optical system 22 functions as a zoom optical system that can change the beam diameter by configuring the first lens 22*a* and the second lens 22*b* to be adjustable in conjunction with each other. Note that the position of the second lens 22B may be adjusted independently relative to the second beam-shaping lens 1B, or may be adjusted together with the position of the second beam-shaping lens 1B.

The third light beam L3 emitted from the second collimating optical system 22 has a light intensity distribution that continuously increases from the outer periphery to the center, similar to the first light beam L1. The third light beam L3 may be a Gaussian light intensity distribution. The second beam-shaping lens 1B is a lens configured in the same manner as the beam-shaping lens 1 illustrated in FIG. 1. The second beam-shaping lens 1B has a third surface containing a smooth-shaped concave surface and a fourth surface including a convex surface substantially similar in shape to the concave surface. The second beam-shaping lens 1B converts the third light beam L3 into a fourth light beam L4 that is a parallel light with a flatter light intensity distribution than that of the third light beam L3. The fourth light beam L4 may have a flat light intensity distribution from the vicinity of the outer periphery of the fourth light beam L4 to the center.

The dichroic mirror 31 configures the combining unit. The dichroic mirror 31 has optical characteristics that reflect light of a specific wavelength emitted from the second light source unit 21 and transmit light in other wavelength ranges. When the light of the specific wavelength is near-infrared light, among the light of the second light beam L2 of white light emitted from the first light source unit 11, most of the light having a wavelength shorter than the near-infrared wavelength passes through the dichroic mirror 31, excluding the portion of the near-infrared wavelength. The fourth light beam L4 that is near-infrared light emitted from the second light source unit 21 is reflected by the dichroic mirror 31.

In one embodiment, the dichroic mirror 31 is positioned at angle of precisely 45° relative to the optical axes of the first beam-shaping lens 1A and the second beam-shaping lens 1B, which are orthogonal to each other, as illustrated in FIG. 5. As a result, the second light beam L2 emitted from the first beam-shaping lens 1A and passing through the dichroic mirror 31 and the fourth light beam L4 emitted from the second beam-shaping lens 1B and reflected by the dichroic mirror 31 are combined. Note that the angles between the optical axes of the first beam-shaping lens 1A and the second beam-shaping lens 1B and the dichroic mirror 31 is not limited to 45°.

The second light beam L2 and the fourth light beam L4, combined by the dichroic mirror 31, are focused by the focusing lens 32 onto the end of the light guide 33, coupled to the light guide 33, and is guided to an endoscope. The second light beam L2 and the fourth light beam L4 guided through the light guide 33 exit from the other end of the light guide 33 and illuminate the biological tissue to be observed.

Figure 8:
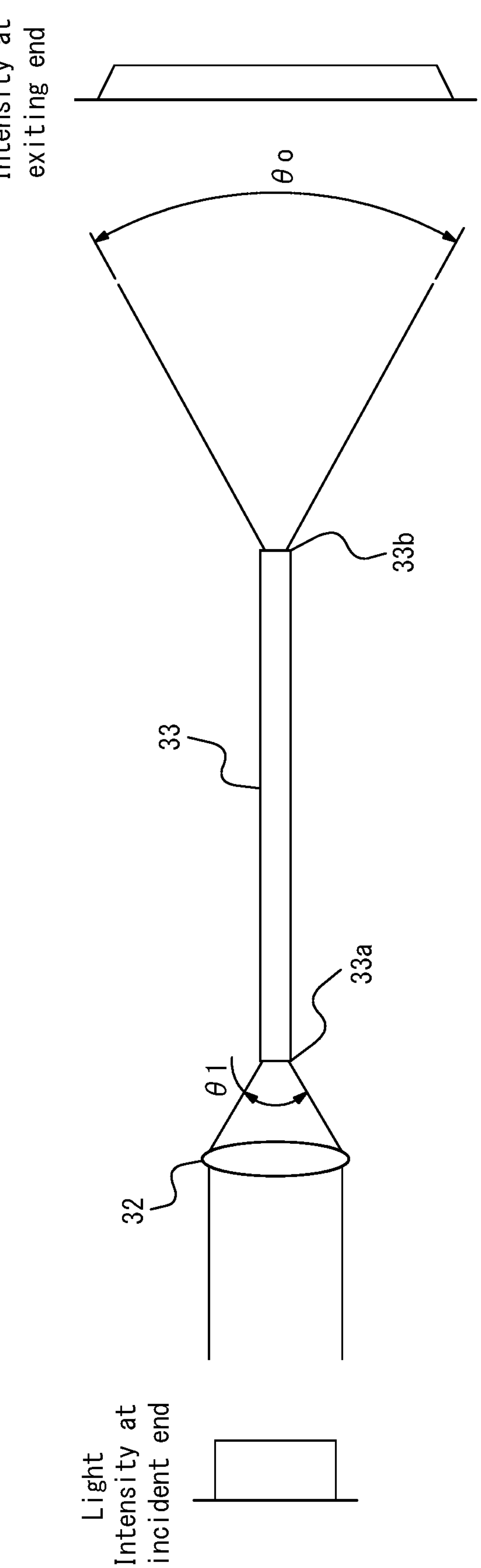
FIG. 8 is a diagram illustrating the light intensity distributions at the incident end and the light intensity distribution at the emission end of a light guide.

The light guide 33 is configured by bundling a number of optical fibers to propagate light. As illustrated in FIG. 8, when light focused by the condenser lens 32 is incident on the light guide 33 from the incident end 33*a*, diverging light exits from the emission end 33*b* of the light guide 33. The convergence angle θi of the light incident on the incident end 33*a* and the divergence angle θo of the light emitted from the emission end 33*b* are approximately equal. Furthermore, as illustrated in FIG. 8, when the light intensity distribution of the light incident on the incident end 33*a* is uniform, the light intensity distribution of the light emitted from the emission end 33*b* is also generally uniform.

The light source device 10 for an endoscope of the present embodiment uses the first beam-shaping lens 1A to make the light intensity distribution of white light emitted from the first light source unit 11 uniform, enabling uniform illumination of a wide area of the tissue surface layer. This enables accurate endoscopic observation and diagnosis with less ununiformity over a wide area of tissue surface layer. Furthermore, the light source device 10 for an endoscope uses the second beam-shaping lens 1B to make the excitation illumination light emitted from the second light source unit 21 uniform, so that the excitation illumination light uniformly illuminates the tissue to be observed. This enables accurate observation with less ununiformity also in fluorescence observation. Furthermore, according to the light source device 10 for an endoscope, a high-power light source is not needed for observing tissues in the outer periphery. Moreover, the light source device 10 for an endoscope can also reduce the risk of damage to some tissues in the center by exposing a wide area of the tissue to intense light for observation of the outer periphery.

The first beam-shaping lens 1A and the second beam-shaping lens 1B used in the present embodiment convert an incident parallel light beam into a light beam with a flatter light intensity distribution while maintaining the light to be parallel light. This is particularly advantageous in the light source device 10 for an endoscope of the present embodiment that uses the dichroic mirror 31 to combine the two light beams. The dichroic mirror 31 has a dependence on incident angle because it uses a dielectric film. Unless the designed incidence angle is used, the dichroic mirror 31 cannot meet the predefined transmission and reflection wavelength characteristics.

In addition, the light source device 10 for an endoscope also includes a zoom optical system that changes the diameter of the illumination light for fluorescent observation in the second collimating optical system 22. If the diameter of the third light beam L3 is reduced in the second collimating optical system 22, the diameter of the fourth light beam L4 is reduced. When the light is reflected by the dichroic mirror 31 and then incident into the light guide 33 by the focusing lens 32, the convergence angle θi at the incident end 33*a* becomes small, as can be seen from FIG. 8. As a result, the divergence angle θo at the emission end 33*b* of the light guide 33 also becomes smaller, thus narrowing the irradiation range of the excitation illumination light in the endoscope. In other words, by adjusting the position of the first lens 22*a* and the second lens 22*b* in the second collimating optical system 22, it is possible to narrow the range of fluorescence observation and increase the intensity of the irradiated excitation light. Accordingly, the light source device 10 for an endoscope enables accurate observation and diagnosis of deep inside biological tissue by illuminating excitation light having high light intensity by narrowing the range of fluorescent observation to a specific location. The user of the light source device 10 for an endoscope can use this function to observe biological tissue with white light while observing a specific area in fluorescent observation.

Furthermore, the light source device 10 for an endoscope aligns and retains the emission side ends of the first optical fiber 212*a* and the second optical fiber 212*b* through the small fiber aperture 213*a* in the ferrule 213, so that the excitation light from the two light sources is emitted in a close proximity. This is advantageous in reducing the size of the light source device 10 for an endoscope, as explained below.

When multiple light sources are used, it is not possible to place all light sources on the optical axis of the collimating optical system. For example, even in the case in FIG. 6, the optical axis of the second collimating optical system 22 is adjusted to coincide with the center of the fiber aperture 213*a*. In this case, the centers of both the first optical fiber 212*a* and the second optical fiber 212*b* are positioned displaced from the optical axis of the second collimating optical system 22.

When light sources are positioned distant from the optical axis of the collimating optical system, their exiting light exits from the collimating optical system at a different angle for each light source. The angle of the exiting light @ is expressed as follows, wherein the distance between the optical axis and the light source is y and the combined focal length of the collimating optical system is F.

$$\Theta=\tan^{-1}(y/F)$$

As mentioned above, if the incidence angle deviates from the specified angle, the dichroic mirror cannot meet the predefined transmission and reflection wavelength characteristics. To reduce the tilt angle Θ of the exiting ray of light, it is necessary to narrow the distance between the optical axis of the collimating optical system and each light source, or to use a collimating optical system with a long focal length. However, the disadvantage of using a collimating optical system with a long focal length is that the entire optical system becomes larger.

For the above reason, in the light source device 10 for an endoscope of the present disclosure, the emission side ends of the first optical fiber 212*a* and the second optical fiber 212*b* are aligned and accommodated in the ferrule 213 having the fiber aperture 213*a* with a small aperture diameter. This allows the distance between the optical axis of the second collimating optical system 22 and the respective center axes of the first 212*a* and second 212*b* optical fibers to be brought closer. Thus, even when the second collimating optical system 22 with a short focal length is used, it is possible to guide the third light beam L3 to the dichroic mirror 31 with a small tilt angle from the default angle of a ray of light. As a result, the size of the second collimating optical system 22 can be reduced, which enables size reduction of the light source device 10 for an endoscope.

As an example, the wavelength of the excitation light emitted from the first light source 211*a* and the second light source 211*b* is assumed to be 785 nm. Furthermore, the first optical fiber 212*a* and the second optical fiber 212*b* are assumed to have a numerical aperture (NA) of approximately 0.5 for light with a wavelength of 785 nm. Furthermore, the first optical fiber 212*a* and the second optical fiber 212*b* have a core diameter of 500 μm and a fiber diameter of 540 μm. When they are inserted into a ferrule with an aperture diameter of 1.2 mm, it is calculated that the second collimating optical system with a combined focal length of 10 mm limits the spread of the incident angles to the dichroic mirror 31 within 3.4°.

Assume that the combined focal length of the second collimating optical system 22 is within 10 mm and the dichroic mirror 31 permits the deviation from the specified incident direction of ±5° or less. Even when some mounting errors of lenses or dichroic mirror are present, when the aperture diameter of the fiber aperture 213*a* accommodating the emission side ends of the first optical fiber 212*a* and the second optical fiber 212*b* in the ferrule 213 is at least 1.2 mm or less, it is possible to keep the spread of the incident angle of the excitation light to the dichroic mirror 31 within a permitted range, as indicated by the above calculation example. This configuration makes it possible to make the light source device 10 for an endoscope smaller.

Although the embodiment according to the present disclosure has been described based on the drawings and examples, it should be noted that a person skilled in the art can easily make various variations or modifications based on the present disclosure. Thus, it should be noted that these variations or modifications are included within the scope of the present disclosure.

The beam-shaping lens and the beam-shaping element of the present disclosure have been described as used in a light source device for an endoscope. However, the beam-shaping lens is not limited to the one used for a light source for an endoscope. The beam-shaping lens of the present disclosure can be applied to various applications that convert the light intensity distribution of a light beam emitted from a light source to a flatter light intensity distribution.

The light source device 10 for an endoscope in the above-described embodiment has a first light source unit 11 that emits white light and a second light source unit 21 that emits excitation light, but the light source device for an endoscope of the present disclosure is not limited to this configuration. For example, the light source device for an endoscope may be configured to have a single light source unit and a corresponding beam-shaping lens. In other words, the beam-shaping lens can be used in endoscopes that perform either the diagnosis of surface tissues using white light or fluorescence observation using light of a particular wavelength range. Alternatively, the light source device for an endoscope may have three or more light source units. Furthermore, the wavelength ranges of three or more light sources may be different from each other.

The light source device 10 for an endoscope of the present disclosure is used for endoscopes. However, a light source device similarly constructed to the light source device 10 for an endoscope of the present disclosure can also be used for microscopes.

In the present disclosure, expressions such as "first" and "second" are identifiers to distinguish the elements being referred to. Elements distinguished by expressions such as "first" and "second" in the present disclosure may be interchangeably numbered. For example, the identifier "first" of the first light source 211*a* can be exchanged with the identifier "second" of the second light source 211*b*. The exchange of identifiers takes place simultaneously. After the exchange of identifiers, the relevant elements are distinguished from each other. The identifiers may be removed. Elements from which the identifiers have been removed are distinguished by their reference symbols. The interpretation of the order of the elements and the presence of identifiers with smaller numbers should not be inferred solely based on the identifiers such as "first" and "second" in the present disclosure.

REFERENCE SIGNS LIST

1 Beam-shaping lens
1A First beam-shaping lens
1B Second beam-shaping lens
2 First surface
2*a* Concave surface
2*b* Outer periphery
3 Second surface
3*a* Convex surface
3*b* Outer periphery
5 Beam-shaping element
10 Light source device for endoscope
11 First light source unit
12 First collimating optical system
21 Second light source unit
211*a* First light source
211*b* Second light source
212*a* First optical fiber
212*b* Second optical fiber
213 Ferrule (optical fiber end retainer)
22 Second collimating optical system (zoom optical system)
22*a* First lens
22*b* Second lens
31 Dichroic mirror (combining unit)
32 Condenser lens
33 Light guide
O Optical axis (central axis)
L1 First light beam
L2 Second light beam
L3 Third light beam
L4 Fourth light beam

The invention claimed is:

1. A light source device for an endoscope comprising:
a first light source unit;
a first collimating optical system that converts light emitted from the first light source unit into a first light beam that is parallel light; and
a first beam-shaping lens comprising a first surface comprising a smooth-shaped concave surface and a second surface comprising a convex surface substantially similar in shape to the concave surface, the first beam-shaping lens converting the first light beam incident on the first surface and having a light intensity distribution that continuously increases from an outer periphery toward a center, into a second light beam that has a flatter light intensity distribution than that of the first light beam,
wherein the first collimating optical system comprises a zoom optical system comprising a first lens having a negative refractive power and a second lens having a positive refractive power, and configured to adjust positions of the first lens and the second lens in conjunction with each other.

2. The light source device for an endoscope according to claim 1, wherein the first light source unit comprises a plurality of light sources that emit light in the same wavelength range, a plurality of optical fibers that guide the light emitted from each of the light sources, and an optical fiber end retainer that aligns and retains emission side ends of the light of the plurality of optical fibers.

3. The light source device for an endoscope according to claim 1, comprising:
a second light source that emits light in a wavelength range different from that of the first light source unit;
a second collimating optical system that converts the light emitted from the second light source unit into a third light beam that is parallel light;
a second beam-shaping lens comprising a third surface comprising a smooth-shaped concave surface and a fourth surface comprising a convex surface substantially similar in shape to the concave surface, the second beam-shaping lens converting the third light beam incident on the third surface and having a light intensity distribution that continuously increases from an outer periphery toward a center, into a fourth light beam that has a flatter light intensity distribution than that of the third light beam;
a combining unit that combines the second light beam exiting from the first beam-shaping lens and the fourth light beam exiting from the second beam-shaping lens; and
a focusing lens that couples the second light beam and the fourth light beam combined at the combining unit, into a light guide that guides the light to an endoscope.

4. The light source device for an endoscope according to claim 3, wherein the combining unit comprises a dichroic mirror.

5. The light source device for an endoscope according to claim 3, wherein the first light source unit comprises a white light source and the second light source unit comprises an excitation light source for fluorescent observation.

6. The light source device for an endoscope according to claim 3, wherein the second collimating optical system comprises a zoom optical system comprising a first lens having a negative refractive power and a second lens having a positive refractive power, and configured to adjust positions of the first lens and the second lens in conjunction with each other.

7. The light source device for an endoscope according to claim 3, wherein the second light source unit comprises a plurality of light sources that emit light in the same wavelength range, a plurality of optical fibers that guide the light emitted from each of the light sources, and an optical fiber end retainer that aligns and retains emission side ends of the light of the plurality of optical fibers.

8. The light source device for an endoscope according to claim 7, wherein a combined focal length of the second collimating optical system is within 10 mm, the combining unit permits a deviation of ±5° or less from a specified incident direction of the fourth light beam exiting from the second beam-shaping lens, and an aperture diameter in the optical fiber end retainer accommodating the emission side ends of the plurality of optical fibers is 1.2 mm or less.

9. An endoscope comprising the light source device according to claim 1.

* * * * *